United States Patent [19]

Jones et al.

[11] Patent Number: 4,872,561

[45] Date of Patent: Oct. 10, 1989

[54] CARBOXY, CARBOALKOXY AND CARBAMILE SUBSTITUTED ISONITRILE RADIONUCLIDE COMPLEXES

[75] Inventors: Alun G. Jones, Newton Centre; Alan Davison, Needham; James Kronauge, Cambridge; Michael J. Abrams, Allston, all of Mass.

[73] Assignees: Massachusetts Institute of Technology; President and Fellows of Harvard College, both of Cambridge, Mass.

[21] Appl. No.: 139,289

[22] Filed: Dec. 29, 1987

Related U.S. Application Data

[62] Division of Ser. No. 771,284, Aug. 30, 1985, Pat. No. 4,735,793.

[51] Int. Cl.$^4$ .................. B65D 69/00; C07C 119/02; C07F 13/00; A61K 49/02
[52] U.S. Cl. .................................. 206/569; 424/1.1; 534/10; 534/14; 558/302
[58] Field of Search .................. 424/1.1; 534/10, 14; 558/302; 206/569

[56] References Cited

U.S. PATENT DOCUMENTS 4,452,774  6/1984  Jones et al. ................... 424/1.1
4,707,544  11/1987  Jones et al. ................... 534/14
4,781,912  11/1988  Zanelli et al. .................. 424/1.1

Primary Examiner—John S. Maples
Attorney, Agent, or Firm—Sewall P. Bronstein; George W. Neuner; Ronald Eisenstein

[57] ABSTRACT

A coordination complex comprising a radionuclide selected from the class consisting of radioactive isotopes of Tc, Ru, Co, Pt and Re and an isonitrile ligand of the formula:

(CNX)R, where X is a lower alkyl group having 1 to 4 carbon atoms, wherein R is selected from the group consisting of COOR$^1$ and CONR$^2$R$^3$ where R$^1$ can be H, a pharmaceutically acceptable cation, or a substituted or unsubstituted alkyl group having 1 to 4 carbon atoms. R$^2$, and R$^3$ can be H, or a substituted or unsubstituted alkyl group having 1 to 4 carbon atoms, and R$^2$ and R$^3$ can be the same of different is disclosed. Kits that can be used to form these complexes are also disclosed.

10 Claims, 9 Drawing Sheets

CARBOXY, CARBOALKOXY AND CARBAMILE SUBSTITUTED ISONITRILE RADIONUCLIDE COMPLEXES

This is a division of co-pending application Ser. No. 771,284, filed on 8/30/85, now U.S. Pat. No. 4,735,793.

This invention was made with government support by way of Department of Energy contracts German Pat. Nos. C02-81EV 10649 and C02-76EV 04115 and the U.S. government has certain rights in the invention.

Jones et al. U.S. Pat. No. 4,452,774 issued June 5, 1984 discloses coordination complexes of isonitrile ligands and radioactive metals, and is incorporated herein by reference. The coordination complexes described therein are useful in visualizing cardiac tissue studying lung function, studying renal excretion, and for imaging bone marrow and the hepatobiliary system. These complexes are useful as diagnostic agents for labelling liposomes or vesicles and selected living cells.

We have now discovered that using isonitrile ligands having the formula:

$$(CNX)R, \quad (I)$$

where X is a lower alkyl group having 1 to 4 carbon atoms, R is selected from the group consisting of $COOR_1$ and $CONR^2R^3$; where $R^1$ can be H, a pharmaceutically acceptable cation, or a substituted or unsubstituted alkyl group having 1 to 4 carbon atoms, $R^2$ and $R^3$ can be H, or a substituted or unsubstituted alkyl group having 1 to 4 carbon atoms, and $R^2$ and $R^3$ can be the same or different, results in a complex having the general advantages of the isonitrile radionuclide complexes of U.S. Pat. No. 4,452,774, but having generally superior properties with respect to liver clearance or lung clearance. Consequently, the complexes of the present invention can allow earlier imaging, and/or better imaging of bodily tissues and organs than their corresponding parent compounds.

Thus, the present invention provides coordination complexes of Tc, Ru, Co, Pt or Re with the above isonitrile ligands of formula I.

DESCRIPTION OF THE INVENTION

The present invention is directed to complexes of a radioactive metal (radionuclide) selected from the class consisting of Tc, Ru, Co, Pt and Re and a carboxylic acid, ester or amide derivative of a lower alkyl isonitrile ligand (also herein referred to as a derived alkyl isonitrile ligand). The isonitrile ligands useful in the present invention disclosed herein have the following general formula:

$$(CNX)R,$$

where X is a lower alkyl group having 1 to 4 carbon atoms, and R is selected from the group consisting of $COOR^1$ and $CONR^2R^3$, where $R^1$ can be H, a pharmaceutically acceptable cation, such as Na+, or a substituted or unsubstituted alkyl group having 1 to 4 carbon atoms, $R^2$ and $R^3$ can be H, or a substituted or unsubstituted alkyl group having 1 to 4 carbon atoms, and $R^2$ and $R^3$ can be the same or different. Preferably, X is a lower aklyl group having 1 to 3 carbon atoms.

Complexes using the present derived alkyl isonitrile ligands typically illustrate faster liver clearance or faster lung clearance when compared to the corresponding parent isonitrile ligand. This generally enables complexes of the present invention to provide better and/or earlier images than the corresponding parent isonitrile ligand. For example, with a heart agent, rapid liver clearance is desirable because it will increase the contrast between the heart and the adjacent liver. Similarly, rapid lung clearance is desirable to improve the contrast between the heart and the lungs by reducing background "noise". Analogously, this rapid clearance enables earlier and/or better images of other tissues and/or organs which are blocked by background noise from the liver and/or lungs. Preferred complexes of the present invention provide optimal tissue uptake as well as faster liver and lung clearance.

Although complexes of this invention can be neutral or positively or negatively charged, the class of lipophilic cationic complexes is presently preferred. However, the complex cannot be too lipophilic and still provide rapid liver and/or lung clearance. Therefore, it is preferred that the total number of carbon atoms in each isonitrile ligand is 12 or less. More preferably, the total number of carbon atoms in each ligand is 10 or less. Most preferably, the total number of carbon atoms in each ligand is 8 or less. When there are 4 carbon atoms in X, it is preferred that R has 5 or less carbon atoms, most preferably, R has 3 or less carbon atoms.

Because of the general availability of supplies of $^{99m}$Tc in clinical laboratories in the form of pertechnetate as well as the desirable half-life and gamma ray energy of this radionuclide, the complexes of the present invention preferably contain $^{99m}$Tc. Additionally, this above-described general availability of supplies of pertechnetate make it convenient to use kits for preparation of various complexes of $^{99m}$Tc.

Therefore, the invention further comprises a kit for using a predetermined quantity of a radionuclide, e.g. $^{99m}$Tc-pertechnetate to prepare a complex as stated above, said kit comprising the isonitrile ligand of the formula (CNX)R and a reducing agent capable of reducing the radioactive metal to form the coordination complex. The components of this kit are sterile and are packaged in a sterile, non-pyrogenic container. Thus, they are ready for admixture with, for example, $^{99m}$Tc pertechnetate to prepare complexes of the present invention.

For purposes of this invention, useful radionuclides are radioactive metals having decay properties that are amenable for use as a tracer.

Counterions that maybe used in the invention include, for example, in the case of cationic complexes, chloride, fluoride, bromide, iodide, hydroxide, sulfate or bisulfate, dihydrogen phosphate, fluoroborate, hexafluorophosphate, etc. Depending upon the particular radionuclide used, the valence state and other conditions for complexing, a particular radioactive metal can have from one to eight isonitrile ligands bonded thereto. As aforesaid, each isonitrile ligand is bonded to the radionuclide through the isonitrile carbon atom. Preferably, the complexes of this invention are kinetically inert, and hence stable products. However, the complexes need only be sufficiently stable for the intended use.

The complexes of the present invention include mixed ligand complexes wherein at least one ligand is a derived alkyl isonitrile. The mixture can include a mixture of isonitrile ligands, as well as other ligands well known to those skilled in the art.

We presently believe that the complex of the present invention which is a homoleptic six coordinate (hexakis) cationic complex having the formula:

[A(CNX)R$_6$]$^+$ in which A is a monovalent radionuclide selected from Tc, or Re, and [(CNX)R] is a monodentate isonitrile ligand, is the most preferred. A suitable counterion such as described above is also present.

The complexes of the present invention can easily be prepared by admixing a salt of the radioactive metal and the isonitrile ligand of the present invention in the presence of a suitable reducing agent, if required, in aqueous media at temperatures from room temperature to reflux temperature or even higher, and are obtainable and isolatable in high yield at both macro (carrier added, e.g. $^{99}$Tc) concentrations and at tracer (no carried added, e.g. $^{99m}$Tc) concentrations of less than $10^{-6}$ molar. In some cases the isonitrile ligand can itself act as the reducing agent thus eliminating the need for an additional reducing agent. Suitable reducing agents, when required or desired, are well known to those skilled in the art. The reaction is generally complete within 2 hours, depending upon the identity of the particular reagents employed. The radiolabelled complex is made in the same way as the corresponding non-radioactive isonitrile complex by simply substituting the desired radionuclide for the corresponding non-radioactive element in the starting materials, except in the case of technetium because all technetium isotopes are radioactive.

In the case of technetium such as, for example $^{99}$Tc or $^{99m}$Tc, a complex in accord with this invention is preferably made by mixing pertechnetate (Tc$^{+7}$) with the desired isonitrile in an aqueous medium, then adding to the reaction mixture an appropriate reducing agent capable of reducing the technetium. Suitable reducing agents include alkali metal dithionites, stannous salts, sodium borohydride, and others well known to the skilled artisan.

The derived alkyl isonitrile technetium complexes of this invention can also be prepared from preformed technetium complexes having oxidation states for technetium of, for instance, +3, +4, or +5, by treating these preformed complexes with an excess of derived alkyl isonitrile ligands under suitable conditions. For example, the technetium-derived alkyl isonitrile complex can also be prepared by reacting the desired isonitrile ligand with the hexakis-thiourea complex of Tc$^{+3}$ or with a technetium-glucoheptonate complex, or the like.

Kits in accord with the present invention comprise a quantity of a reducing agent for reducing a preselected radionuclide. Preferably, such kits contain a predetermined quantity of a derived alkyl isonitrile ligand and a predetermined quantity of a reducing agent capable of reducing a predetermined quantity of a preselected radionuclide. The isonitrile ligand and reducing agent are generally provided in sealed, sterilized containers.

In one embodiment of the invention, a kit for use in making the complexes of the present invention from a supply of $^{99m}$Tc such as the pertechnetate solution in isotonic saline available in most clinical laboratories includes the desired quantity of a selected derived alkyl isonitrile ligand to react with a selected quantity of pertechnetate, and a reducing agent such as sodium dithionite or stannous chloride in an amount sufficient to reduce the selected quantity of pertechnetate to form the desired complex.

A molar excess of the derived alkyl isonitrile ligand, typically 600% molar excess or more, and an excess of reducing agent, can be used in the complexing reaction to ensure maximum yield of the desired complex from the technetium. Following the reaction, the desired complex can be separated from the reaction mixture, if required, by crystallization or precipitation or by conventional chromatography or ion exchange chromatography.

The following specific examples are intended to illustrate more fully the nature of the present invention. They should not be construed as limiting its scope, which is set forth in the claims.

EXAMPLE 1

Methylisocyanoacetate

To a solution of glycine methylester-hydrochlodride (10.13 g, 0.08 mol) in formic acid (95%, 30 ml) was added a solution of sodium formate in formic acid (5.5 g in 10 ml). The solution was heated to dissolve the salts and then stirred for 2 hours at 40° C. The white precipitate (NaCl) was removed by filtration through Celite TM 545. To the filtrate was added acetic anyhydride (30 ml) and formic acid (50 ml) in a 300 ml round-bottomed flask equipped with a condenser and magnetic stirrer. It was stirred for 2 hours, when the initial reaction was over the mixture was refluxed for 40 hours. And a further aliquot (20 ml) of the acetic anyhydride formic acid mixture (1:2 v/v) and refluxed for 16 hours. The above procedure was repeated once more. The solvents were removed in vacuo at room temperature. The product methylformamidoacetate was separated from the residue by vacuum distillation (142°-145° C., 15 mm Hg). The recovered yield was 7.12 g (76%).

$^1$H NMR: δ3.7 (s, 3H, Me); δ4.0 (d, J=4 Hz —CH$_2$); δ6.4 (vb, 1H —NH—); δ8.03 (s, 1H —CHO).

The formamide, vide supra, (7.11 g, 0.06 mol) was dissolved in $CH_2Cl_2$ (100 ml) and placed in a 500 ml triple-necked round-bottomed flask. The solution was purged with argon and cooled to $-30°$ C. To the flask was added $Me_3N$ (Me=methyl) (35 ml) dissolved in $CH_2Cl_2$ (75 ml). The mixture was cooled and stirred while adding dropwise a solution of trichloromethyl chloroformate (diphosgene) (6.01 g, 0.030 moles) in $CH_2Cl_2$ (50 ml). The solution turned color from tan to brown. The mixture was allowed to warm slowly to room temperature and then heated to reflux for 30 minutes. The reaction mixture was treated with ammonium hydroxide (30%, 100 ml). The $CH_2Cl_2$ layer was separated. The aqueous layer was extracted three times with $CH_2Cl_2$ (50 ) and the extracts combined. The $CH_2Cl_2$ extract was dried over sodium sulfite. The volume was reduced under vacuum and the product, methylisocyanoacetate, separated by vacuum distillation ($64°-65°$ C., 10 mm of Hg). Yield, 1 ml. $^1$H NMR: $\delta 3.83$ (s, 3H—OMe); $\delta 4.23$ (s, 2H —$CH_2$—). IR: $V_{NC}$ 2182 $cm^{-1}$; $V_{CO}$ 1782 $cm^{-1}$.

EXAMPLE 2

Hexakis carbomethoxymethylisonitrile Technetium (I) Hexafluorophosphate

Hexakis(thiourea-S)technetium (III) (Abrams, M. J., et al, *Inorg. Chem.*, 23:3284–3288 (1984); Abrams, M. J., et al, *J. Lab. Comp. Radiopharm.*, 14:1596 (1982)) tetrafluoroborate (0.42 g) was dissolved in MeOH (50 ml), the system purged with argon, and methylisocyanoacetate (150 ul) was added to the clear red solution. The mixture was heated to reflux (30 minutes), and the volume reduced to ca. 10 ml in vacuo. The residue was titrated with a solution of $NH_4PF_6$ in MeOH (5 ml). Addition of $Et_2O$ (Et=ethyl) (10 ml) caused the crude solid to separate.

Recrystallization from acetone/ether gave white crystals (0.24 g, 43.8%).

$^1$H NMR: $\delta 3.7$ (s, 3H, ml); $\delta 4.58$ (b, s, 2H —$CH_2$—). FAB(+)MS: M/Z 693.

A Kit For The Preparation Of No Carrier Added (NCA) Hexakis carbomethoxymethylisonitrile Technetium Cation From Generator Eluant ($^{99m}TcO_4-$)

To a 5 ml serum vial containing $Na_2S_2O_4$ (4-5 mg) was added EtOH (0.5 ml) and methylisocyanoacetate (20 ul) (uls microliters). The vial was sealed and $^{99m}Tc$ pertechnetate in normal saline generator eluant (0.5 ml) injected into the vial. The vial and contents were shaken for 5 seconds and heated to 60° C. for 1 hour. HPLC and reversed phase TLC showed that the yield of the complex was 93%.

EXAMPLE 3 t-Butylisocyanoacetate

This ester was prepared similarly to the methylisocyanoacetate. The glycine t-butylesterhydrochloride was prepared from glycine suspended in t-ButOH (But=butyl) and treated with anhydrous HCl. The amine esterhydrochloride was recrystallized from methylethyl ketone/hexane. The intermediate t-butylformamidoacetate was distilled at $115°-120°$ C., 1 mm of Hg.

$^1$H NMR: $\delta 1.67$ (s, 9H, $C(CH_3)_3$); $\delta 4.03$ (d, 2H, J+4 HZ —$CH_2$—); $\delta 6.67$ (bs, 1H, —NH—); $\delta 8.08$ (s, 1H, —CHO).

t-butylisocyanoacetate distilled at $54°-56°$ C., 0.4 mm Hg $^1$H NMR: $\delta 1.67$ (s, 9H, —$C(CH_3)_3$); $\delta 4.05$ (s, 2H, —$CH_2$—).

IR: $V_{NC}$, 2162 $cm^{-1}$; $V_{CO}$, 1762 $cm^{-1}$.

Hexakis Carbo-t-butoxymethylisonitrile Technetium (I) Tetrafluoroborate

This salt was made in a similar manner to the hexakis-carbomethoxymethylisonitrile technetium derivative except that t-ButOH was used as a solvent and the product chromatographed on neutral alumina with $CH_2Cl_2$. Concentration of the eluant and the addition of hexane ether (1:1 v/v) gave white crystals on cooling (5° C.).

FAB(+)MS: M/Z 945

The kit for the NCA preparation of $^{99m}Tc$-hexakis carbo-t-butoxymethylisonitrile technetium was similar to that for hexakis carbomethoxymethylisonitrile technetium except that the vial contents were heated at 45° C. for 75 minutes for >95% yield (HPLC and TLC).

EXAMPLE 4

Methyl-2-aminoisobutyrate hydrochloride

The methyl ester hydrochloride was made by the treatment of 2-aminobutyric acid with anhydrous HCl in MeOH.

M.pt.: $157°-158°$ C.

Methyl-2-formamidoisobutyrate

The methyl-2-aminoisobutyrate hydrochloride was converted by N-formylation using the formic acid, acetic anhydride procedure in 60% yield.

B.pt. $86°-89°$ C., 0.8 mm Hg.

$^1$H NMR: $\delta 1.6$ (s, 6H, $C(CH_3)_2$); $\delta 3.73$ (s, 3H, OMe); $\delta 70$ (s, b, 1H, NH); $\delta 8.28$ (s, 1H, CHO).

Methyl-2-isocyanoisobutyrate was obtained by dehydration of the formamide with diphosgene.

B.pt.: $70°-71°$ C., 26 mm Hg.

$^1$H NMR: $\delta 1.68$ (s, 6H, $C(CH_3)_2$); $\delta 3.83$ (2, 3H, OMe).

IR: $V_{NC}$ 2141 $cm^{-1}$; $V_{CO}$ 1752 $cm^{-1}$.

Kit Formulations For The NCA Preparation Of $^{99m}Tc$-Hexakis-1-carbomethoxyisopropylisonitrile Technetium (I)

(a) To a 5 ml serum vial containing $Na_2S_2O_4$ (5.5 mg) was added EtOH (0.5 ml) and methyl-2-isocyanoisobutyrate (20 ul). The vial was sealed and $^{99m}Tc$ pertechnetate normal saline generator eluant (0.5 ml) injected into the vial. The vial was heated (60° C.) for 50 minutes. HPLC and TLC (reversed phase) showed the yield of the complex was 97%.

(b) To a 5 ml serum vial was added EtOH (0.5 ml) and methyl-2-isocyanoisobutyrate (20 ul). The vial was sealed. It was then injected with a reconstituted technetium $^{99m}Tc$ glucoheptate sodium kit (Glucoscan™ (0.5 ml) and allowed to stand 2 hours at 23° C. HPLC and TLC showed that the yield of the complex was 84%.

(c) To a 5 ml serum vial was added stannous tartrate (2.15 mg), MeOH (0.8 ml), and methyl-2-isocyanoisobutyrate (20 ul). The vial was sealed and injected with $^{99m}Tc$-pertechnetate normal saline generator eluant (0.2 ml) and allowed to stand for 60 minutes. The yield was 70%.

EXAMPLE 5

Isocyanoacetamide

Gaseous $NH_3$ was bubbled through a solution of methylisocyanoacetate (6.2 g) and MeOH (10 ml) for 15 minutes. The contents were stirred for 15 minutes, then concentrated. The addition of $Et_2O$ cause the isocyanoacetamide to separate as white crystals which were collected and dried in vacuo. The yield was 1.4 g (25%).

Anal Calcd for $C_3H_4N_2O_2$ C, 54.66, H, 4.70; N, 1822; Found C, 53.49; H, 4.70; N 1775.

IR: $V_{CN}$ 21114 cm$^{-1}$, $V_{CO}$ 1650 cm$^{-1}$.

Kit For The Preparation Of NCA $^{99m}$Tc Hexakis-carbomethoxyisonitrile Technetium (I)

To a 5 ml septum vial was added $Na_2S_2O_4$ (5.5 mg) and isocyanoacetamide (11 mg). The vial was sealed prior to the injection (1 ml) of generator eluant ($^{99m}$Tc pertechnetate in normal saline). The contents were heated at 100° C. for 1 minute. The yield was 97% (HPLC).

Preparation Of NCA Hydrolysed Hexakis-carbomethoxymethylisonitrile Technetium To a $^{99m}$Tc reconsitituted kit of NCA hexekis carbomethoxymethylisonitrile technetium (I) was added aqueous sodium hydroxide (0.5 ml, 0.5M) and the solution was heated at 60° C. for 15 minutes. The vial contents were neutralized with dilute HCl (0.5M).

EXAMPLE 6

Ethyl-3-aminopropanoate hydrochloride

The ethyl-3-aminopropanoate hydrochloride was made by the treatment of 3 aminopropanic acid with anhydrous HCl in EtOH.

Ethyl-3-formamidopropanoate

The ethyl-3-aminopropanoate hydrochloride was converted by N-formylation using the formic acid, acetic anhydride procedure in 59% yield.

B.pt. 131°–136° C., 15 mm Hg.

Ethyl-3-isocyanopropanoate was obtained by dehydration of the formamide with diphosgene. The yield was 65%.

B.pt.: 70°–71° C., 19 mm Hg.

Kit Formulation For The NCA Preparation Of $^{99m}$Tc-Hexakis-2-carboethoxyethylisonitrile Technetium (I)

To a 5 ml serum vial containing $Na_2S_2O_4$ (5.7 mg) was added EtOH (0.5 ml) and ethyl-3-isocyanopropanoate (20 ul). The vial was sealed and $^{99m}$Tc pertechnetate normal saline generator eluant (0.5 ml) injected into the vial. The vial was heated (60° C.) for 50 minutes, HPLC and TLC (reversed phase) showed the yield of the complex was better than 98%.

EXAMPLE 7

Preparation of Injection Media (a) The NCA preparations of the $^{99m}$Tc complexes can be diluted with normal saline to 25% EtOH, and then filtered (Sartorius Minisart TM NML). Suitable aliquots of these solutions can be used for biological evaluation.

(b) For those situations which required a pure preparation free of the reactants, the following procedure can be used. After the reconstitution with $^{99m}$Tc the contents of the kit are diluted 4 to 1 with water and then eluted through a prewetted Water Associates Sep-Pak TM $C_{18}$ cartridge. The radiolabel is retained in the cartridge, and is washed with saline (5 ml) followed by ethanol/saline (10 ml, 45/55, v/v) and is eluted with mixture of 85% EtOH, 5% ammonium acetate (0.5M) and 10% saline (0.15M) (1.5 ml). The eluant is diluted with saline (0.15M) and filtered through a 0.2 micron Sartorius Minisart TM NML filter to yield a sterile, pyrogen free solution suitable for biological evaluation.

Extraction of the Product

This step may be used with the above syntheses to provide a pure sample of the isonitrile complex freed from the other materials in the syntheses.

The solution was transferred to a separatory funnel (50 ml) and twice extracted with methylene chloride (3 ml). The organic phase was twice washed with isotonic saline (5 ml) and then transferred to a siliconized round-bottomed flask (50 ml) fitted with a vacuum adaptor. The solvent was removed in vacuo, aided by heating with an infra-red lamp. The flask was washed first by addition of ethanol (100 ul) followed by saline (1 ml). The solution was then ready for administration to animals after assay by HPLC, the complex being in the form of a solution in a physiologically acceptable non-toxic carrier.

EXAMPLE 8

Scintigrapic Imaging Procedure in Animals

Rabbits

Two rabbits were anesthetized with sodium pentobarbital and injected via an ear vein with 3–8 mCi of $^{99m}$Tc-isonitrile complex. One rabbit was imaged using a gamma camera equipped with a pinhole collimator positioned directly over the chest. Three minute static images were acquired at 5, 10, 20, 20, 40, 50 and 60 minutes post injection. A second rabbit was used to investigate the relative whole body distribution of activity for 60 minutes post-injection. Immediately post-injection, 300 thousand count images were acquired in the following sequence of projections: chest, anterior heart, whole body, anterior heart, left lateral whole body, anterior heart, lateral heart, anterior heart.

Swine

Swine were sedated with intramuscular injections of Ketamine and acepromazine, and anesthetized with sodium pentobarbital. The animals were positioned for anterior image acquisition over the chest under a low energy, high resolution collimator and injected with 10–12 mCi $^{99m}$Tc-isonitrile complex via a leg vein. The liver was covered with a lead shield, and three minute images were acquired at 5, 10, 20, 30, 40, 50 and 60 minutes post-injection.

Dogs

After anesthetization with sodium pentobarbital, dogs were injected with 25 mCi of $^{99m}$Tc and positioned for anterior chest image acquisition using a pinhole collimator. Again, three minute images were obtained at 5, 10, 20, 30, 40, 50 and 60 minutes post-injection.

Figure 1:
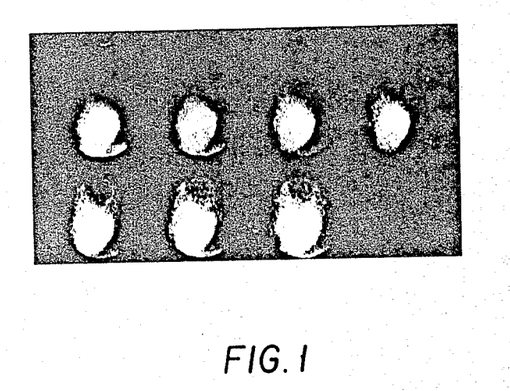
FIG. 1 is a scintigraphic image of a rabbit injected with a complex of $^{99m}$Tc with a carbomethoxyisopropylisonitrile ligand in accord with the present invention.
Figure 2:
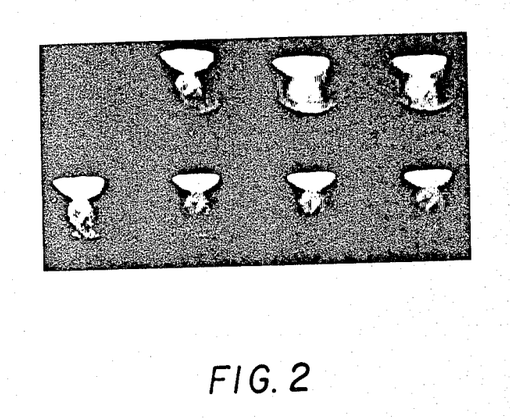
FIG. 2 is a scintigraphic image of a pig injected with a complex of $^{99m}$Tc with a carbomethoxyisopropylisonitrile ligand in accord with the present invention.

Representative scintigraphic images from 5 to 60 minutes post-injection for rabbits and pigs are shown in FIGS. 1 and 2, respectively.

EXAMPLE 9

Rabbits were anesthetized with Ketamine and Nembutal ™ and positioned beneath a gamma camera to allow continuous collection of data including a chest and abdomen view. 1 mCi of the test agent as specified below was injected via an ear vein and data collected continuously at 60 second intervals for 60 minutes. Curves were generated by drawing regions of interest over selected tissues and normalizing to counts per minute per pixel.

The following complexes of $^{99m}Tc$ with methyl isonitrile ligands were injected into rabbits: $CNCH_2R$ where R was —H, —$COOCH_3$, —$COOC_2H_5$, —$COO^nC_3H_7$, —$COO^iC_4H_9$ and —$CONH_2$. The effect of these substitutions on the clearance curve of the complex through the liver is set forth below in Table 1.

TABLE 1

Liver Activity for Complexes of $^{99m}Tc$ Formed with Ligands of the Type $CNCH_2R$

| Ligand $CNCH_2R$ | | $t_{max}$ (min) | $t_{\frac{1}{2}}$ (min) |
|---|---|---|---|
| R = | —H | 14 | 88 |
| | —$COOH_3$ | 1 | 37 |
| | —$COOC_2H_5$ | 3 | 12 |
| | —$COO^nC_3H_7$ | 2 | 11 |
| | —$COO^iC_4H_9$ | 5 | 25 |
| | —$CONH_2$ | 1 | 13 |

Liver activity for ethyl isonitrile and some of its derivatives are described in Table 2. While Table 3 shows the liver activity for isopropylisonitrile and some of its derivatives.

TABLE 2

Liver Activity for the Complexes of $^{99m}Tc$ Formed with Ligands of the Type $CNCH(R)CH_3$ or $CNCH_2CH_2R$

| | Ligand | | $t_{max}$ (min) | $t_{\frac{1}{2}}$ (min) |
|---|---|---|---|---|
| (a) | $CNCH(R)CH_3$ | | | |
| | R = | —H | 2 | 270 |
| | | —$COOCH_3$ | 2 | 45 |
| | | —$COOC_2H_5$ | 4 | 12 |
| (b) | $CNCH_2CH_2R$ | | | |
| | R = | —H | 2 | 270 |
| | | —$COOCH_3$ | 7 | 85 |
| | | —$COOC_2H_5$ | 2 | 17 |

TABLE 3

Liver Activity for the Complexes of $^{99m}Tc$ Formed with Ligands of the Type $CNC(CH_3)_2R$

| Ligand | | $t_{max}$ (min) | $t_{\frac{1}{2}}$ |
|---|---|---|---|
| $CNC(CH_3)_2R$ | | | |
| R = | —H | 5 | 98 |
| | —$COOCH_3$ | 3 | 35 |
| | —$COOC_2H_5$ | 5 | 22 |
| | —$COO^nC_3H_7$ | 2 | 39 |
| | —$COOH$ | 1 | 6 |
| | —$CONH_2$ | 2 | 44 |

The data clearly shows that the clearance of the derived compounds of the present invention is substantially faster than that of the corresponding parent compound. All the data in the above three tables are from dynamic camera studies in rabbits by the procedure described above. The time of maximum activity in the liver post injection is "$t_{max}$", while "$t_{\frac{1}{2}}$" is the apparent half life of the clearance curve from $t_{max}$. The latter data is an estimate based on data collected to 60 minutes after administration. This assumes a simple exponential curve with time, although more extensive studies might indicate more components are actually present.

FIG. 3 is a comparison of counts per minute per pixel (pix) over time in minutes for complexes of $^{99m}Tc$ with isonitrile ligands of the formula $CN(CH_2)R$, where R is:
 (a) —H,
 (b) —$COOCH_3$
 (c) —$COOC_2H_5$;
 (d) —$COO^nC_3H_7$; and
 (e) —$COO^iC_4H_9$.

Figure 3A:
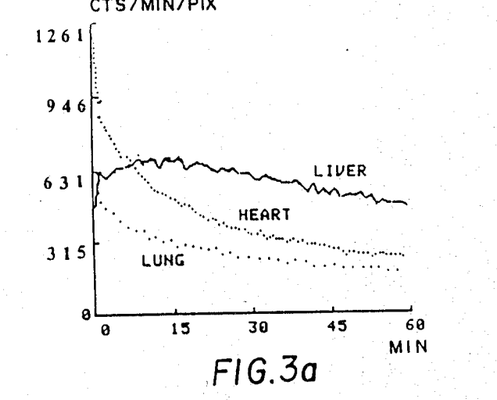
FIGS. 3a–3c is a comparison of counts per minute per pixel over time for complexes of $^{99m}$Tc with methyl isonitrile ligands, and derivatives of methyl isonitrile of the present invention.
Figure 3B:
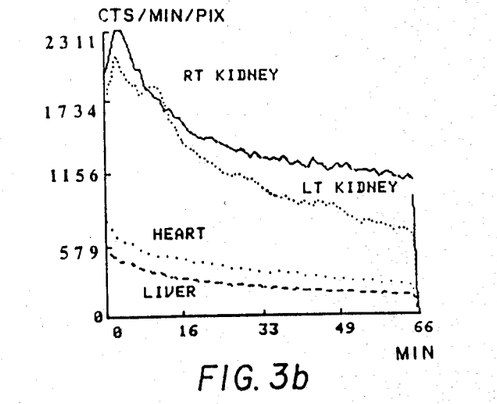
Figure 3C:
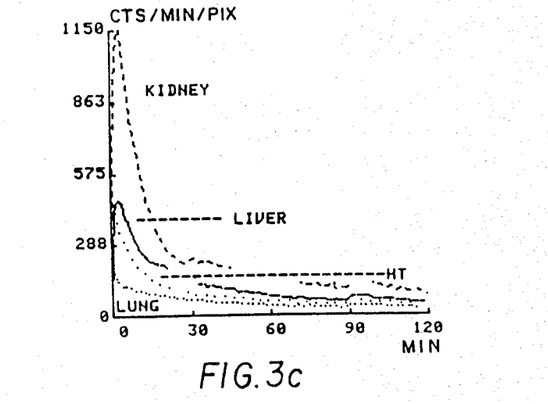
Figure 3D:
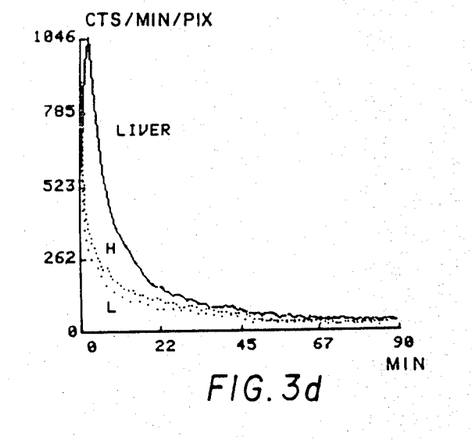
Figure 3E:
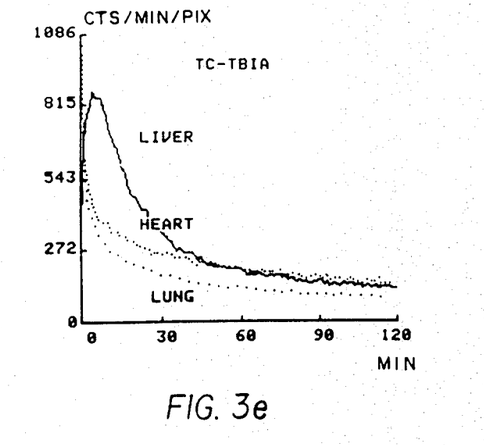
Figure 4A:
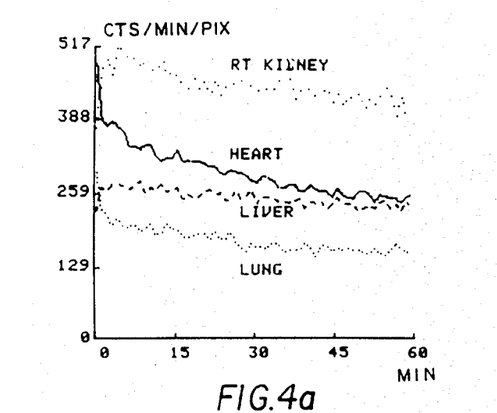
FIGS. 4a–4e is a comparison of counts per minute per pixel over time for complexes of $^{99m}$Tc with ethyl isonitrile ligands and derivatives of ethyl isonitrile of the present invention.
Figure 4B:
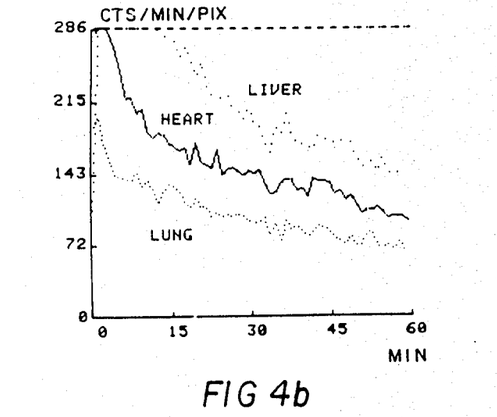
Figure 4C:
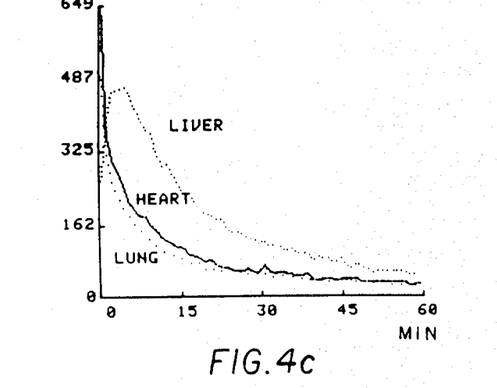
Figure 4D:
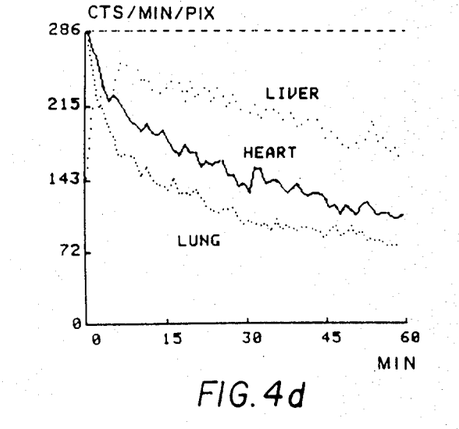
Figure 4E:
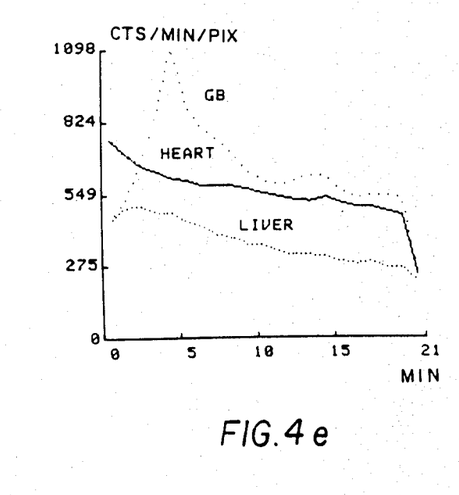
Figure 5A:
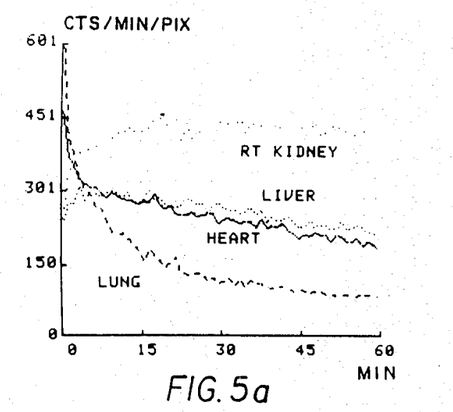
FIGS. 5a–5f is a comparison of counts per minute per pixel over time for complexes of $^{99m}$Tc with isopropyl isonitrile ligands and derivatives of isopropyl isonitrile of the present invention.
Figure 5B:
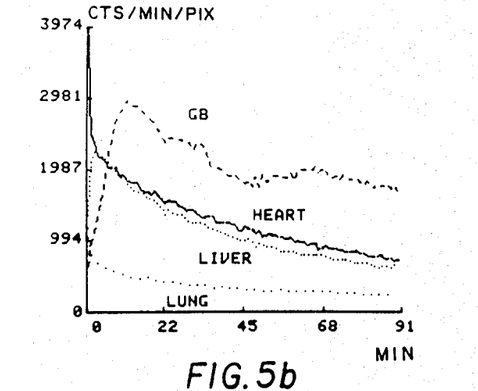
Figure 5C:
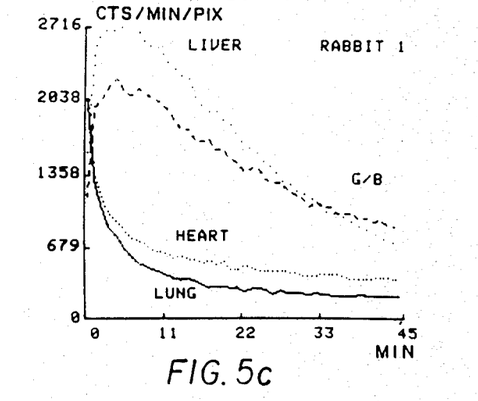
Figure 5D:
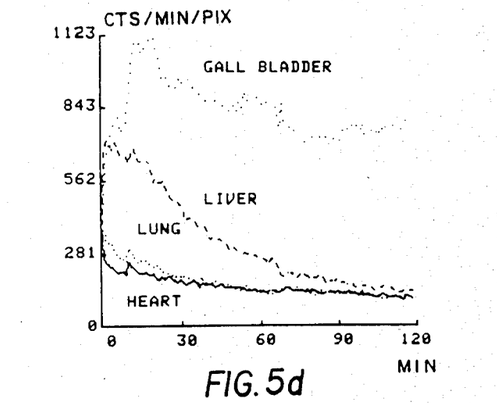
Figure 5E:
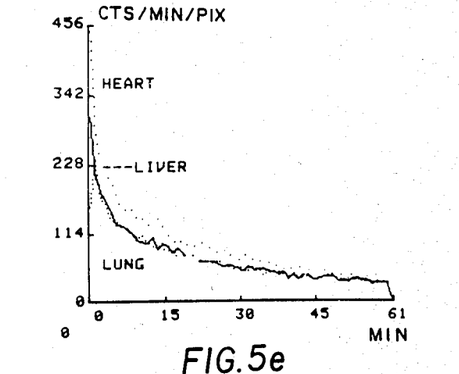
Figure 5F:
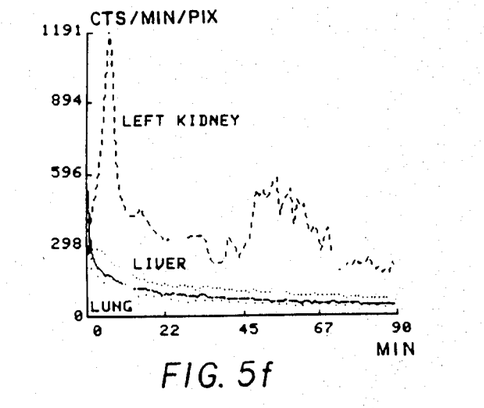

The complexes were prepared, injected and imaged as described above.

FIG. 4 is a comparison of counts per minute per pixel over time (minutes) for complexes of $^{99m}Tc$ with isonitrile ligands of the formula:
 (a) $CNCH_2CH_3$
 (b) $CNCH(R)CH_3$, where R is —$COOCH_3$;
 (c) $CNCH(R)CH_3$, where R is —$COOC_2H_5$;
 (d) $CNCH_2CH_2(R)$, where R is —$COOCH_3$;
 (e) $CNCH_2CH_2(R)$, where R is —$COOC_2H_5$.

FIG. 5 is a comparison of counts per minute per pixel over time (minutes) for complexes of $^{99m}Tc$ with isonitrile ligands of the formula $CNC(CH_3)_2R$, where R is:
 (a) —H;
 (b) —$COOCH_3$
 (c) —$COOC_2H_5$;
 (d) —$COO^nC_3H_7$;
 (e) —$COOH$; and
 (f) —$CONH_2$.

These figures show that complexes containing the derived alkyl isonitrile ligand have faster liver and/or lung clearance than the corresponding parent compound. Consequently, the complexes of the present invention can allow earlier imaging and/or better imaging of bodily tissues and organs.

Figure 6A:
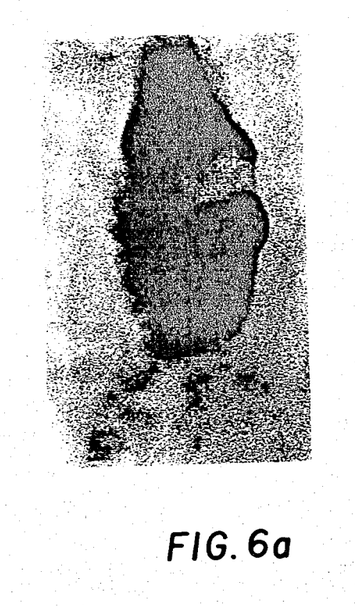
FIGS. 6a–6b is a scintigraphic image of a rabbit injected with a complex of $^{99m}$Tc with a carbomethoxyisopropylisonitrile ligand in accord with the present invention.
Figure 6B:
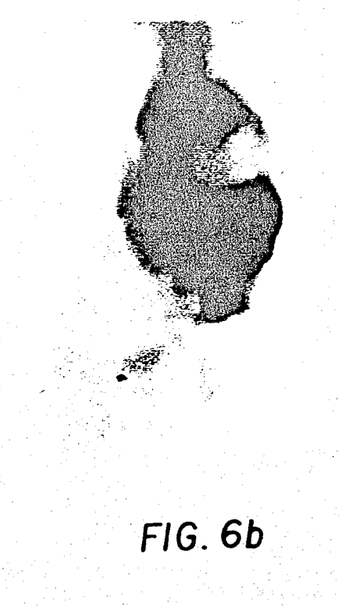
Figure 7A:
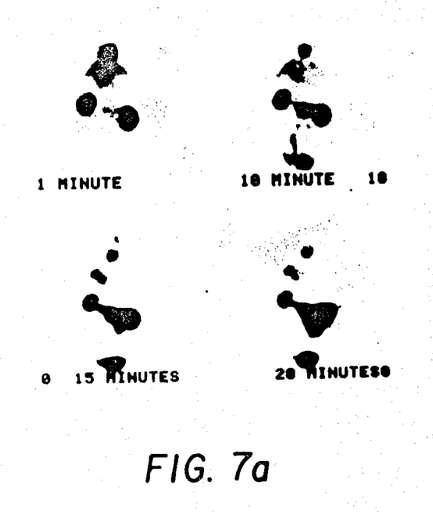
FIGS. 7a–7b is a scintigraphic image of a rabbit injected with a complex of $^{99m}$Tc-2-carboethoxyethylisonitrile in accord with the present invention.
Figure 7B:
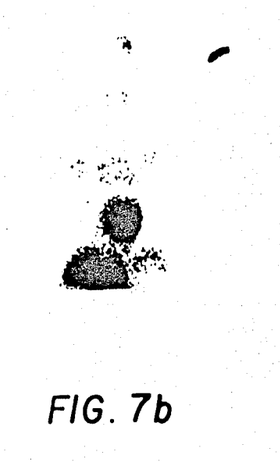

For example, coordination complexes of the present invention containing ligands of carbomethoxyisopropylisonitrile or 2-carboethoxyethylisonitrile appear to be particularly useful for imaging the heart. Because of rapid lung clearance there is very good to excellent resolution of the myocardium at five minutes after injection of complexes containing ligands of carbomethoxyisopropylisonitrile in rabbits when imaged. Although the liver uptake results in background noise that initially prevents clear visualization of the apex of the heart, by 20 minutes after injection, there has been sufficient liver clearance to allow excellent resolution of the apex. FIG. 6(a) is a scintigraphic image of a rabbit injected with a complex of $^{99m}Tc$-carboethoxyisopropylisonitrile at 5 minutes after injection, while FIG. 6(b) is a scintigraphic image of the same rabbit at 15 minutes after injection. FIG. 7(a) is a scintigraphic image of a rabbit injected with a complex of $^{99m}Tc$-2-carboethoxyethylisonitrile at 1, 10, 15 and 20 minutes post injection. FIG. 7(b) is a scintigraphic image of a rabbit injected with the above complex at 31 minutes post-injection. The heart is at (A), the gall bladder at (B) and the site of injection at (C). The interpretation of these images is known to the person of ordinary skill in this field. While reading of these images is somewhat qualitative, the above described $^{99m}Tc$-carboethoxyethylisonitrile compound has resulted in excellent images in both animal and human tests.

This invention has been described in detail including the preferred embodiments thereof. However, it will be appreciated that those skilled in the art, upon consideration of this disclosure, may make modifications and improvements within the spirit and scope of this invention.

We claim:

1. A kit for preparing a coordination complex of (a) an isonitrile ligand of the formula:

$$CN-X-R$$

where X is a lower alkyl group having 1 to 4 carbon atoms, and R is selected from the group consisting of $COOR^1$ and $CONR^2R^3$ where $R^1$ can be H, a pharmaceutically acceptable cation, or a substituted or unsubstituted alkyl group having 1 to 4 carbon atoms, $R_2$ and $R_3$ can be H, or a substituted or unsubstituted alkyl group having 1 to 4 carbon atoms, and $R^2$, and $R^3$ can be the same or different, and (b) a radionuclide selected from the class consisting of radioactive isotopes of Tc, Ru, Co, Pt and Re, said kit comprising a predetermined quantity of said isonitrile ligand and a predetermined quantity of a reducing agent capable of reducing a predetermined quantity of a preselected one of said radionuclides to form said complex, wherein said isonitrile ligand and said reducing agent are sterile and non-pyrogenic.

2. A kit as claimed in claim 1 wherein said preselected radionuclide is an isotope of Tc.

3. A kit as claimed in claim 1 wherein said preselected radionuclide is an isotope of Re.

4. A kit as claimed in claim 1 wherein said isonitrile ligand and reducing agent are contained in a sealed, sterilized container.

5. A kit as claimed in claim 2 wherein said preselected radionuclide is an isotope of Tc.

6. A kit as claimed in claim 4 wherein said preselected radionuclide is an isotope of Re.

7. A kit for converting a supply of a radionuclide to a coordination complex of a lower alkyl isonitrile ligand of the formula:

$$CN-X-R,$$

where X is a lower alkyl group having 1 to 4 carbon atoms, wherein R is selected from the group consisting of $COOR^1$ and $CONR^2R^3$ where $R^1$ can be H, a pharmaceutically acceptable cation, or a substituted or unsubstituted alkyl group having 1 to 4 carbon atoms, $R^2$, and $R^3$ can be H, or a substituted or unsubstituted alkyl group having 1 to 4 carbon atoms, and $R^2$ and $R^3$ can be the same or different, and a radioactive metal selected from the class consisting of radioactive isotopes of Tc, Ru, Co, Pt and Re, said kit comprising a predetermined amount of said lower isonitrile ligand and a supply of a reducing agent capable of reducing the radionuclide, wherein said isonitrile ligand and said reducing agent are sterile and non-pyrogenic.

8. The kit of claim 7 wherein the radionuclide is technetium.

9. A kit as claimed in claim 8 in which said reducing agent is selected from the class consisting of dithionites and stannous salts.

10. A kit as claimed in claim 8 wherein said isonitrile ligand and reducing agent are contained in a sealed, sterilized container.